(12) United States Patent  
Ross et al.

(10) Patent No.: US 8,983,578 B2
(45) Date of Patent: Mar. 17, 2015

(54) SYSTEM AND METHOD FOR TRANSDUCER PLACEMENT IN SOFT-FIELD TOMOGRAPHY

(75) Inventors: Alexander Seth Ross, Albany, NY (US); Jeffrey Michael Ashe, Gloversville, NY (US)

(73) Assignee: General Electric Company, Niskayuna, NY (US)

( * ) Notice: Subject to any disclaimer, the term of this patent is extended or adjusted under 35 U.S.C. 154(b) by 232 days.

(21) Appl. No.: 13/406,236

(22) Filed: Feb. 27, 2012

(65) Prior Publication Data

US 2013/0225985 A1 Aug. 29, 2013

(51) Int. Cl.
*A61B 5/00* (2006.01)
*A61B 5/053* (2006.01)

(52) U.S. Cl.
CPC .................................. *A61B 5/053* (2013.01)
USPC .......................................... 600/425; 600/407

(58) Field of Classification Search
USPC .................................................. 600/407, 425
See application file for complete search history.

(56) References Cited

U.S. PATENT DOCUMENTS

| | | | |
|---|---|---|---|
| 5,588,429 A | 12/1996 | Isaacson et al. | |
| 5,807,251 A | 9/1998 | Wang et al. | |
| 5,919,142 A | 7/1999 | Boone et al. | |
| 6,236,886 B1 | 5/2001 | Cherepenin et al. | |
| 7,206,630 B1 | 4/2007 | Tarler | |
| 7,711,418 B2 | 5/2010 | Garber et al. | |
| 7,865,236 B2 | 1/2011 | Cory et al. | |
| 2004/0243018 A1 | 12/2004 | Organ et al. | |
| 2005/0107716 A1 | 5/2005 | Eaton et al. | |
| 2009/0234244 A1 | 9/2009 | Tanaka | |
| 2010/0059274 A1* | 3/2010 | Ives et al. | 174/71 R |
| 2012/0166127 A1* | 6/2012 | Ross | 702/104 |
| 2013/0096425 A1* | 4/2013 | Uutela et al. | 600/425 |

FOREIGN PATENT DOCUMENTS

| | | |
|---|---|---|
| EP | 1000580 A1 | 5/2000 |
| EP | 2228009 A1 | 9/2010 |
| GB | 2257530 A | 1/1993 |
| WO | 2010112825 A2 | 10/2010 |

OTHER PUBLICATIONS

Search Report and Written Opinion from corresponding EP Application No. 13155968.4-1657 dated Jun. 6, 2013.

* cited by examiner

*Primary Examiner* — Peter Luong
(74) *Attorney, Agent, or Firm* — Melissa K. Dobson

(57) ABSTRACT

A system and method for transducer placement in soft-field tomography are provided. One system includes a plurality of transducers configured for positioning at a surface of an object in a non-soft-field tomography configuration. The system also includes an interface and a processor communicating with the plurality of transducers via the interface. The processor is configured to perform soft-field sensing using soft-field data acquired by the plurality of transducers.

25 Claims, 4 Drawing Sheets

SYSTEM AND METHOD FOR TRANSDUCER PLACEMENT IN SOFT-FIELD TOMOGRAPHY

BACKGROUND

Soft-field sensing, such as Electrical Impedance Tomography (EIT) (also referred to as Electrical Impedance Spectroscopy (EIS)), diffuse optical tomography, elastography, and related modalities may be used to measure the internal properties of an object, such as the electrical properties of materials comprising internal structures of an object (e.g., a region of a human body). For example, in EIT systems, an estimate is made of the distribution of electrical conductivities of the internal structures, such as within a patient. These EIT systems reconstruct the conductivity and/or permittivity of the materials within the area or volume based on an applied excitation (e.g., current) and a measured response (e.g., voltage) acquired at a surface of the area or volume. Visual distributions of the estimates can then be formed.

The EIT measurements may be obtained by applying excitations, which are often very small electrical currents or voltages, using for example skin-contacting electrodes, and measuring the resulting voltages or currents on the same or on different skin-contacting electrodes. The excitations are typically pre-computed and applied to a configuration of transducers coupled to a surface of an object, which is highly dependent on a configuration of the transducers. Presently, the use of EIT electrodes requires a dedicated transducer set in a predetermined geometry, such as a circumferential belt of electrodes surrounding the thorax. Attaching sets of electrodes in predetermined geometries is often problematic in clinical settings where the patient cannot be manipulated appropriately. Further, the need for dedicated electrode arrays presents an additional clinical burden to the caregiver, cost burden to the hospital, insurer, and/or patient, and results in additional discomfort to the patient.

BRIEF DESCRIPTION

In accordance with an embodiment, a soft-field tomography sensing system is provided that includes a plurality of transducers configured for positioning at a surface of an object in a non-soft-field tomography configuration. The soft-field tomography sensing system also includes an interface and a processor communicating with the plurality of transducers via the interface. The processor is configured to perform soft-field sensing using soft-field data acquired by the plurality of transducers.

In accordance with another embodiment, a method for soft-field sensing is provided. The method includes positioning a plurality of transducers at a surface of an object in a non-soft-field tomography configuration and obtaining measured signals from all or a subset of the plurality of transducers. The method further includes performing soft-field sensing using the measured signals acquired by the plurality of transducers.

In accordance with yet another embodiment, a computer readable storage medium for performing soft-field tomography using a processor is provided. The computer readable storage medium includes instructions to command the processor to obtain measurement signals from all or a subset of a plurality of transducers positioned at a surface at an object in a non-soft-field tomography configuration and perform soft-field tomography using the measurement signals acquired by the plurality of transducers.

DETAILED DESCRIPTION

Figure 1:
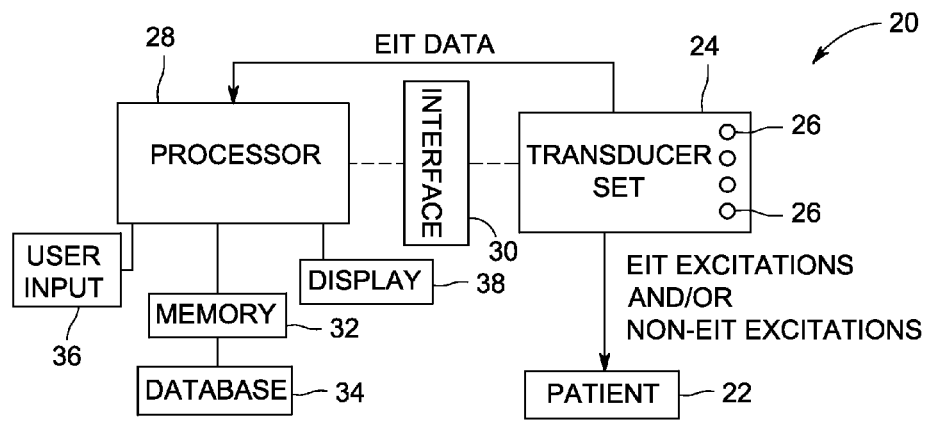
FIG. 1 is a block diagram illustrating an impedance measurement system formed in accordance with one embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, circuits or memories) may be implemented in a single piece of hardware or multiple pieces of hardware. It should be understood that the various embodiments are not limited to the arrangements and instrumentalities shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and methods that use transducers, for example electrodes, in one or more non-soft-field tomography configurations. The transducers may be positioned in the non-soft-field tomography configuration(s) and provide soft-field sensing and/or soft-field tomography, such as for acquiring Electrical Impedance Tomography (EIT) measurements, also referred to as Electrical Impedance Spectroscopy (EIS) measurements. In some embodiments, non-soft-field sensing transducer sets, such as non-EIT transducer sets may be used, for example, electrocardiography (ECG or EKG) transducer sets, electroencephalography (EEG) transducer sets, or other patient-contacting transducer sets (e.g., conventional transducer sets and/or configurations of electrodes, such as in ECG or EKG configurations). It should be noted that the transducer sets may be used to acquire soft-field sensing measurements and/or non-soft-field sensing measurements, such as ECG measurements, EEG measurements or respiration measurements, among others.

In various embodiments, the non-soft-field sensing transducer sets and the different configurations of electrodes in non-soft-field sensing configurations include different types of transducer sets and configurations that are not soft-field transducer sets or transducers in soft-field sensing configurations. For example, non-EIT electrodes or electrodes in a non-EIT configuration (also referred to as non-EIT configured electrodes) in some embodiments include electrodes that are not positioned circumferentially around an object (e.g., thorax or head of a patient), but instead are positioned in a different clinically accepted or clinically relevant configuration, such as in an ECG or EKG configuration. Thus, in various embodiments, the transducers are positioned in an arrangement defined for use in acquiring measurements other than soft-field sensing measurements (e.g., EIT or EIS measurements). Merely for example, in one embodiment, a transducer configuration is provided such that the transducers are not positioned in a spaced apart configuration circumferentially around a patient. As other examples, soft-field configurations include linear arrays, rectangular arrays, circular arrays, cylindrical arrays and/or spherical arrays. Different examples of implementations of soft-field configurations include strips, patches/sheets, belts/bands/cuffs, vests/harnesses, caps and/or cups/cradles/cages. Accordingly, in some embodiments, a non-soft-field tomography configuration includes transducers that are not in an arrayed structure (e.g., a grid that covers a large contiguous area of the object to be measured).

Additionally, in various embodiments, different numbers or combinations of non-EIT configured electrodes (e.g., ECG electrodes) may be used, for example, to pre-compute optimized EIT excitations and to estimate a reconstruction geometry as described in more detail herein.

By practicing at least one embodiment, transducers already attached at or to the patient for other monitoring applications (or in a configuration for other monitoring applications) may be used for soft-field sensing, such as EIT monitoring or other soft-field tomography. For example, ECG or EEG electrodes may be used in pre-defined electrode locations for ECG or EEG to acquire EIT data.

It should be noted that although various embodiments may be described in connection with an EIT system having particular components or performing particular operations, the various embodiments may be implemented in connection with any system that is capable of performing soft-field sensing, such as measuring different properties of an object (e.g., a portion of a patient), for example, electrical impedance, optical scattering or thermal conductivities of the object, among other properties.

One embodiment of a soft-field tomography sensing system is illustrated as an impedance measurement system 20 as shown in FIG. 1, which may be a transducer-based system, for example, an electrode-based system, such as a patient monitor that may form part of an ECG or EEG monitoring device or an impedance cardiography module. However, the impedance measurement system 20 may also be an EIT system or other separate unit. Moreover, the various embodiments may be implemented in connection with different types of soft-field tomography systems, such as Electrical Impedance Spectroscopy (EIS), Electrical Impedance Tomography (EIT), Diffuse Optical Tomography (DOT), Near InfraRed Spectroscopy (NIRS), thermography, elastography, microwave tomography or microwave spectroscopy, and related modalities.

It should be appreciated that the various embodiments may be used in any system capable of performing soft-field sensing or acquiring impedance measurements. It also should be noted that as used herein, "soft-field sensing" or "soft-field tomography" refers generally to any tomographic or multidimensional extension of a tomographic method that is not "hard-field sensing" or "hard-field tomography".

The impedance measurement system 20 may be used to obtain, for example, electrical impedance measurements of an object, illustrated as a patient 22, such as EIT measurements, as well as non-EIT measurements (e.g., ECG or EEG measurements). In the illustrated embodiment, the impedance measurement system 20 includes a transducer set 24, which may include a plurality of transducers 26 (e.g., an electrode set having a set of wires and electrode contacts). In one embodiment the plurality of transducers 26 is a plurality of electrodes positioned at or proximate to a surface of the patient 22. In a healthcare application (e.g., patient monitoring), the positioning may include attaching the transducers 26 (e.g., electrodes) of the transducer set 24 to the skin of the patient 22 in a non-soft-field tomography configuration, for example, a non-EIT configuration. In various embodiments, as described in more detail herein, the transducer set 24 is positioned in an ECG or EEG configuration.

It should be noted that any number of transducers 26 may be provided in the transducer set 24 and different configurations may be used. Moreover, the shape and/or size of the transducers 26 may be changed as desired or needed. It also should be noted that other types of transducers may be used to generate different types of excitations, for example, in addition to current, other sources of excitation include voltage, magnetic fields or radio-frequency waves, among others. Thus, the transducers 26 also may be surface-contacting electrodes, standoff electrodes, capacitively coupled electrodes, antennas, ultrasound transducers, and coils (e.g., conducting coils), among others. For example, the transducers 26 may be positioned on the surface of the patient 22 (e.g. electrodes, thermal sources, ultrasound transducers), near the surface of the patient 22 (e.g., radiofrequency antenna), or penetrating the surface of the patient 22 (e.g., needle electrodes).

The transducers 26 may be positioned at a surface of the patient 22 in different arrangements and may be driven in different configurations. For example, the transducers 26 may be electrodes of the transducer set 24 and positioned at a surface of the patient 22 using one of a plurality of standard ECG locations (e.g., Lead I, Lead II or Lead III ECG configurations) and have different numbers of electrodes, for example, twelve electrodes, five electrodes or three electrodes, among others. As another example, the transducers 26 may be electrodes of the transducer set 24 and positioned at a surface of the patient 22 using one of a plurality of standard EEG locations, which may have different numbers of wires or electrodes such as based on a 10-20 system. In various embodiments, different non-soft-field configurations may be used, for example, (i) an ECG configuration, such a 1, 3, 5, 12 and/or 15-lead configuration, (ii) a body surface potential mapping configuration, (iii) an EEG configuration, such as a 10-20, Duke, and/or sub-hairline montages configuration and/or (iv) an EMG configuration.

However, in other embodiments, different positioning of the transducers 26 in non-standard ECG locations may be provided (e.g., sub-axillary configurations). Additionally, combinations of the different positioning arrangements may be used. As other non-limiting examples of modifications or variations, a configuration similar to the Lead II configuration may be provided, but with the right arm transducers 26 placed on the back of the shoulder (Lead II Back configuration).

It should be noted that the frequency of the applied excitation (e.g., electrical current or voltage) to the transducers 26 may be, for example, 10 kHz for EIT measurements. However as should be appreciated, other frequencies may be used, such as for non-EIT measurements or other EIT measurements. It also should be noted that one or more of the transducers 26 may be a ground reference or a reference for current return and noise cancellation purposes.

Referring again to FIG. 1, the impedance measurement system 20 also includes a processor 28 (e.g., a computing device). The processor 28 sends instructions to drive the transducer set 24 and receive responses therefrom (e.g., measured responses such as measured voltages or currents). In various embodiments, an interface 30 is provided to provide connection and communication between the processor 28 and the transducer set 24. It should be noted that the interface 30 may allow for connection of one or more different types of transducer sets 24, which may be connected as the same time or at different times. It should be noted that the interface 30 may be a separate physical interface or may form part of or be incorporated with the processor 28.

The impedance measurement system 20 further includes a memory 32 coupled to the processor 28, which may have access to or have stored therein one or more databases 34. For example, the database(s) 34 in various embodiments include sets of excitations and pre-computed responses for each of the plurality of different transducer sets 24 and/or configurations of transducers 26 as described in more detail herein. The selection of the excitations and pre-computed responses may be performed manually, for example, by an operator or automatically based on the selected or connected transducer set 24. In some embodiments, excitations and/or predicted responses may be dynamically computed.

The impedance measurement system 20 also includes a user input 36 and a display 38. The user input 36 may include, for example, a keyboard, mouse, etc. allowing an operator to provide inputs to the processor 28. The display 38 may display the results determined from the EIT data or non-EIT data, which may be displayed simultaneously, concurrently or separately.

Figure 2:
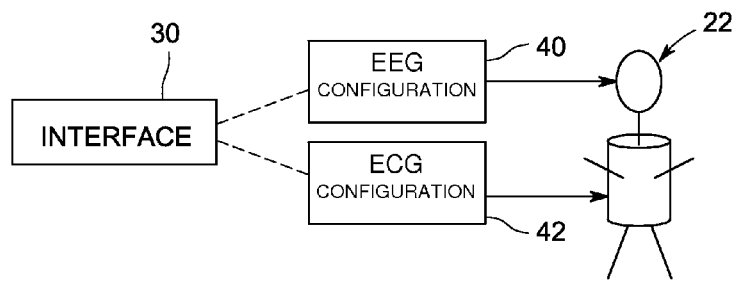
FIG. 2 is a simplified block diagram illustrating an interface arrangement in accordance with one embodiment.

As shown in FIG. 2, various embodiments provide the interface 30 that allows interfacing to the transducer set 24, which may be arranged or positioned in different configurations. For example, the transducer set 24 may be provided in an EEG configuration 40 or an ECG configuration 42. In these configurations, the processor 28 (shown in FIG. 1) may acquire through the interface 30 EEG data or ECG data based on non-EIT measurements (e.g., the patient body generates non-EIT excitations, EEG excitations, and/or ECG excitations that are passively measured or recorded, as standard EEG or ECG measurements) and/or EIT data based on EIT excitations as described in more detail herein.

Figure 3:
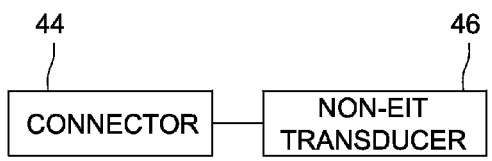
FIG. 3 is a simplified block diagram illustrating a data acquisition configuration in accordance with one embodiment.

Variations and modifications may be provided using different configurations or placements of the transducer set 24. For example, as shown in FIG. 3, a connector 44 may be provided to allow connection of a set of non-EIT transducers 46 (e.g., ECG or EEG electrode set) such as to the interface 30 (shown in FIGS. 1 and 2) or may form part of the interface 30. In this embodiment, the non-EIT transducers 46 are positioned in a non-EIT configuration (e.g., ECG or EEG configuration) to acquire non-EIT data, as well as EIT data. It should be noted that the non-EIT data and the EIT data may be acquired simultaneously, concurrently or sequentially. Additionally, it should be noted that all or a subset of the transducers 26 (shown in FIG. 1) in the set of non-EIT transducers 46 may be used for EIT data acquisition, or generally, any type of soft-field tomography data acquisition or sensing. Additionally, it should be noted that in some embodiments, one or more transducers 26 may be added to the non-EIT transducers 46, such as to an ECG or EEG transducer set 24 as described herein.

Figure 4:
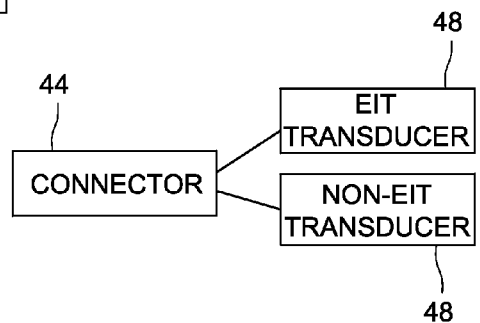
FIG. 4 is a simplified block diagram illustrating a data acquisition configuration in accordance with another embodiment.

It also should be noted that different transducers 26 may be provided at the same or different locations of the patient 22, such that data may be acquired for more than one modality concurrently. For example, as shown in FIG. 4, in addition to the non-EIT transducers 46, a set of EIT transducers 48 may also be provided and connected to the connector 44. Accordingly, the non-EIT transducers 46 and EIT transducers 48 may be used simultaneously, concurrently or sequentially.

Figure 5:
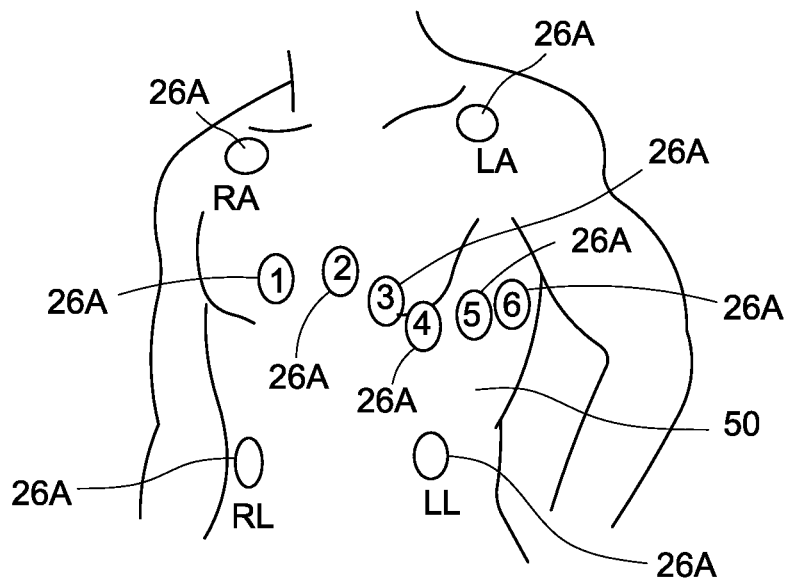
FIG. 5 is a diagram illustrating transducer placement in accordance with an embodiment.

Merely for illustration, the transducers 26 may be provided as electrodes and positioned in standard ECG locations to acquire ECG data and/or EIT data, wherein there is a single electrode at each location with no split between current driving and voltage measuring electrodes, such that the single electrode configuration supports "2-wire" impedance measurements. However, it should be noted that in these standard ECG location there are no electrodes on the back of the patient, such that there are only front-side electrodes. The standard ECG locations include, for example, a standard 3-lead ECG configuration (RA, LA, LL, RL), a standard 5-lead ECG configuration (RA, LA, LL, RL and V (chest)) and a standard 12-lead configuration (RA, LA, LL, RL, V1, V2, V3, V4, V5, V6) as illustrated in FIG. 5.

Figure 6:
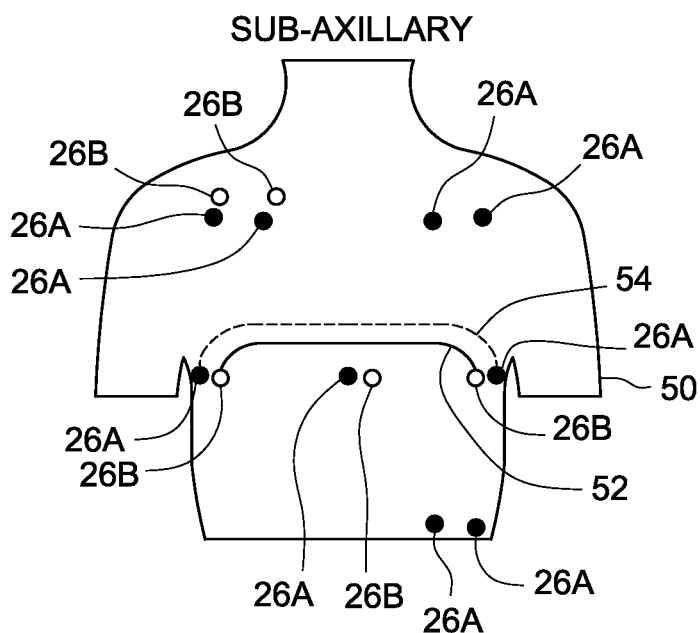
FIG. 6 is a diagram illustrating transducer placement in accordance with another embodiment.
Figure 7:
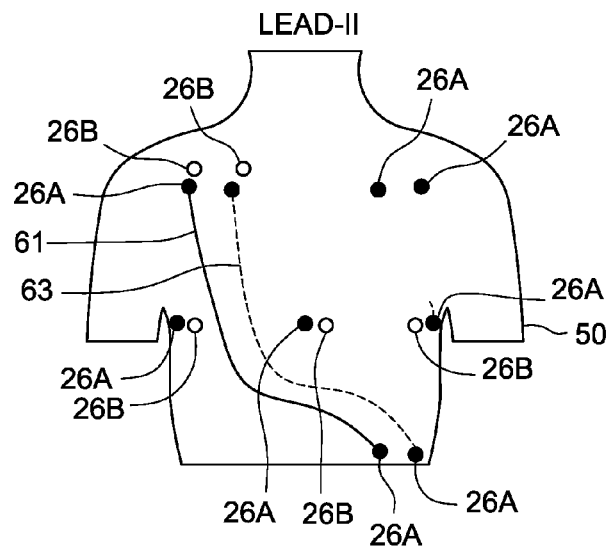
FIG. 7 is a diagram illustrating transducer placement in accordance with another embodiment.

Variations and modifications are contemplated. For example, as shown in FIGS. 6 and 7, EIT type configurations are provided wherein two separate electrodes are integrated in the same patch (illustrated as pairs of electrodes), providing the ability to apply current through one electrode and measure voltage on the other in a "4-wire" impedance measurement. In various embodiments, for example, a set of eight electrodes are placed on the thorax with two electrodes nearby each other in each of the traditional ECG locations including the Right Arm, Left Arm, Right Leg, and Left Leg locations. However, different electrode configurations may be provided. In particular, FIG. 6 illustrates a sub-axillary electrode placement configuration in accordance with one embodiment and FIG. 7 represents a Lead 11 electrode placement configuration, both on a human thorax 50. It should be noted that the front electrodes are identified by the transducers 26a and the back electrodes are identified by the transducers 26b. It also should be noted that the solid line represents an exemplary current path and the dashed line represents a corresponding exemplary measured voltage.

In this illustrative embodiment, the single transducer 26 or one transducer 26 of each pair of transducers 26 drives a small AC current (e.g., 60 µA) at a carrier frequency (e.g., 10 kHz) and the same transducer 26 or the other transducer 26, respectively, of each pair does not drive current. The current path is represented by path 52 in FIG. 6. Thereafter, voltage measurements are performed for all or a subset of the transducers 26 including the current driving transducers 26 and the non-current driving transducers 26. The voltage measurement path is illustrated by path 54 in FIG. 6.

In the various configurations, the transducers 26 are driven or excited to acquire non-EIT data and EIT data. When acquiring non-EIT data, the transducers 26 acquire non-EIT signals, for example, ECG or EEG signals that are passively acquired from a patient. When acquiring EIT data, EIT excitations are generated. In particular, geometries identified by pre-existing clinical transducer placements are assumed and used to pre-compute an optimal or approximately optimal set of excitations The transducer configuration is also used to analytically or numerically pre-compute a set of expected or predicted responses to the excitations. The sets of excitations and predicted responses are stored in the database 34 (shown in FIG. 1) from which an appropriate configuration is selected, such as at the bedside of the patient 22 (shown in FIG. 1) being monitored. The database selection may be performed manually by a clinician, or may be automatic based on the selected ECG, EEG, or other detection by the patient monitor. Thus, the placement of the transducer set 24 (shown in FIG. 1) is used to determine the excitations and predicted response, such as using a thoracic geometry with an ECG electrode configuration and/or a head geometry with a sub-hairline or 10-20 EEG electrode configuration.

Figure 8:
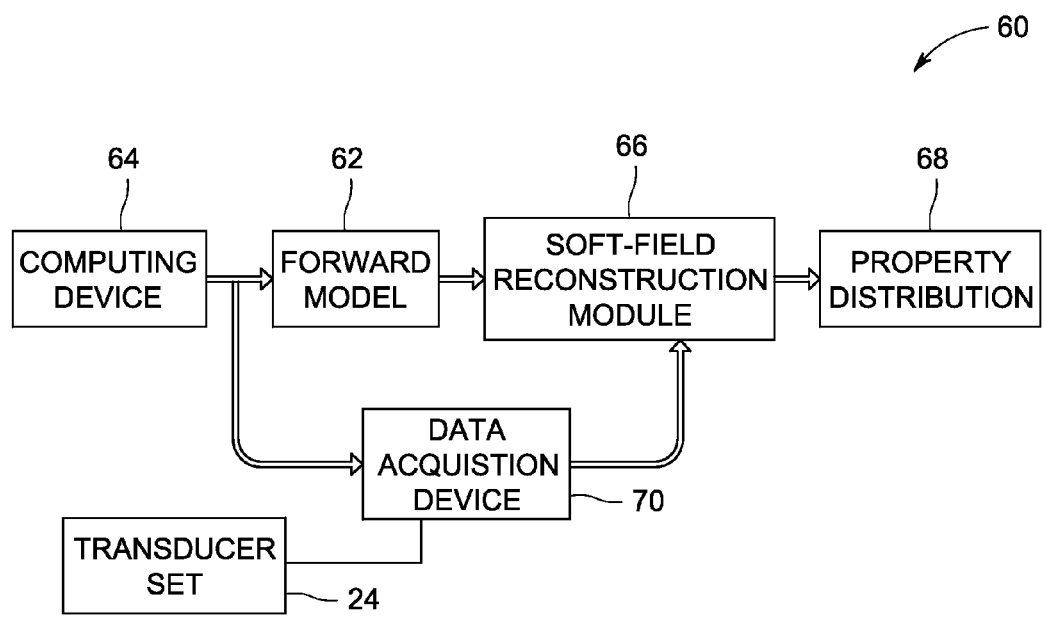
FIG. 8 is a block diagram illustrating soft-field tomography information flow in accordance with various embodiments.
Figure 9:
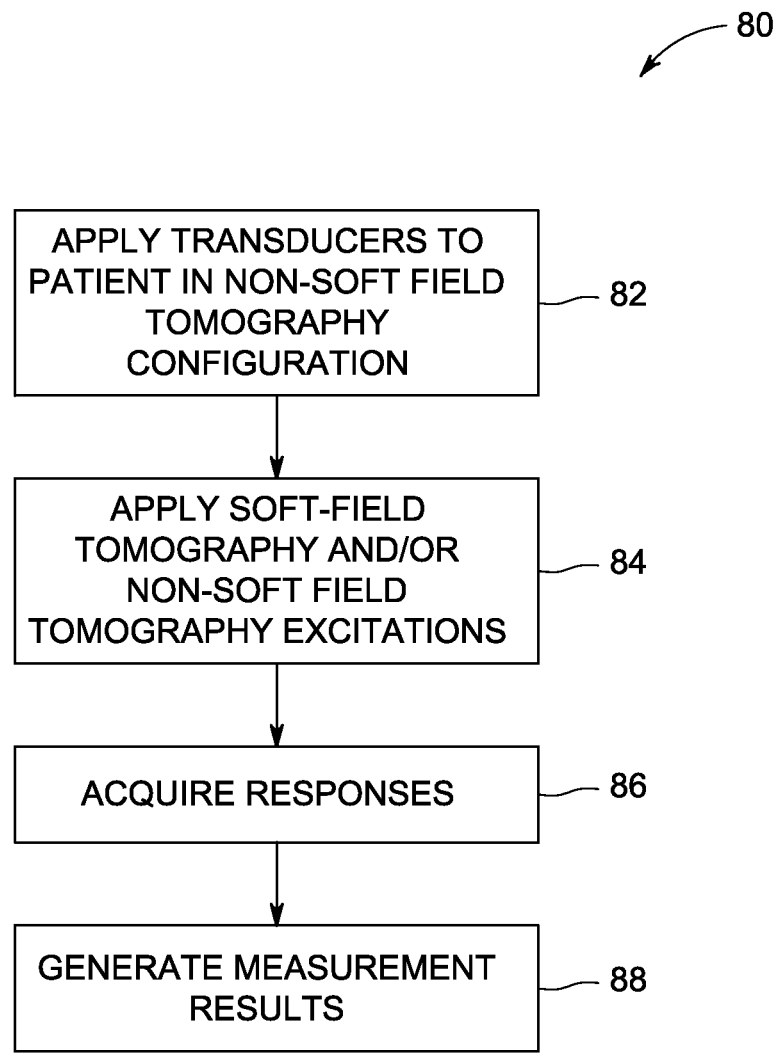
FIG. 9 is a flowchart of a method for performing soft-field tomography in accordance with various embodiments.

For example, in various embodiments, the impedance measurement system 20 computes a response of the patient 22 to the applied excitation. In particular, an exemplary EIS information flow 60 is illustrated in FIG. 8. In particular, a forward model 62 is used based on excitations from a computing device 64, to predict voltages (predicted data), which are provided to a soft-field reconstruction module 66, which may be implemented as part of the processor 28 (shown in FIG. 1). In one embodiment, an inverse problem relating the measured responses (e.g., measured signals) from a data acquisition device 70, the predicted responses, the applied excitations (e.g., applied by the transducer set 24), and the electrical conductivity distribution inside of the patient 22 being tested or interrogated is solved by the soft-field reconstruction module 66 using any suitable soft-field reconstruction technique. It should be noted that the data acquisition device 70 may be, for example, a module or component that may be embodied as part of the computing device 64 and/or the transducer set 24

The excitations are applied to the patient 22 (shown in FIG. 1) by the transducer set 24, which may include the transducers 26 (shown in FIG. 1) and other excitation and measurement components, and thereafter measured signals (measured data) are communicated to the soft-field reconstruction module 66. The soft-field reconstruction module 66 then performs reconstruction using various embodiments to generate, for example, an estimate of the property distribution 68, such as the impedance distribution, to identify properties of interest for the patient 22 (or other object), such as to identify regions of interest within the patient 22 or other temporal features. It should be noted that the various components may be physically separate components or elements or may be combined. For example, the soft-field reconstruction module 66 may form part of the impedance measurement system 20 (as illustrated in FIG. 1).

Using various embodiments, soft-field reconstruction may be provided using the transducers 26 provided in non-EIT configuration of transducers (e.g., patient-contacting electrodes in an EEG or ECG configuration) that perform EIT measurements. Thus, different excitation patterns, for example, numerous types of current excitation patterns may be used as desired or needed. For example, the transducers 26 may be driven with different phase shifts. Thus, in operation, the transducers 26 may be used to deliver electrical current continuously or optionally modulated such that excitations may be applied across a temporal frequency range (e.g., 1 kHz to 1 MHz) at or proximate to the surface of the patient 22 to generate an electromagnetic (EM) field within the patient 22. The resulting surface signals, for example, voltages (real, imaginary or complex) on the transducers 26 may be measured to determine an electrical impedance (e.g. electrical conductivity or permittivity distribution).

It should be noted that the transducers 26 may be formed from any suitable material used to establish a desired excitation. For example, if the transducers 26 are electrodes, the transducers 26 may be formed from one or more metals such as copper, gold, platinum, steel, silver, and alloys thereof. Other exemplary materials for forming the transducers 26, when the transducers 26 are electrodes, include non-metals that are electrically conductive, such as a silicon based materials used in combination with micro-circuits. In one embodiment, the transducers 26 are formed from silver-silver chloride to be attached to the patient 22. Additionally, the transducers 26 may be formed in different shapes and/or sizes, for example, as rod-shaped, flat plate-shaped, or needle-shaped structures. It should be noted that in some embodiments, the transducers 26 are insulated from one another. In other embodiments, the transducers 26 can be positioned in direct ohmic contact with an object or capacitively coupled to the object. It should be noted that the transducers 26 may be embodied as different structures, for example, microwave antennas, optical sources (e.g., a semiconductor device with a lens), ultrasound transceivers, or thermal sources, among others.

It also should be noted that the transducers 26 may be, for example, any suitable ECG or EEG electrode. For example, in some embodiments, the transducers 26 are standard ECG electrodes having a surface area of about 1 square centimeter (sq. cm). However, different sized and shaped electrodes may be used, such as larger electrodes having a surface area of about or at least 70 sq. cm, where an increase in surface area may provide an increase in signal-to-noise ratio.

Various embodiments and methods generally use multiple electrical measurements (for example electrical impedance measurements that are obtained from the plurality of transducers 26). It should be noted that although the measurement signals are illustrated as electrical conductivity measurements of the patient 22, different measurements, such as different voltage, current, magnetic field, optical signal, radio-frequency (RF) wave, thermal field, mechanical deformation, ultrasound signal, or electrical impedance or permittivity measurements, among others, may be made.

Thus, the use of ECG, EEG or other non-EIT patient-contacting electrodes may be used for soft-field sensing or data acquisition, such as to acquire EIT data as described herein. In operation, for example, in an Intensive Care Unit (ICU), Emergency Department (ED), and/or other patient monitoring settings, electrodes, for example ECG electrodes, are attached to the patient. Using the pre-existing electrodes, soft-field sensing or data acquisition is provided.

Various embodiments provide a method 80 as shown in FIG. 8 for performing soft-field sensing or soft-field tomography. In particular, the method 80 includes applying transducers to a patient at 82. In various embodiments, the transducers are a non-soft-field sensing transducer set, such as a non-EIT transducer set, for example ECG or EEG electrode sets that are applied to a patient in a non-soft-field sensing, such as a non-EIT configuration (e.g., defined ECG or EEG configuration). In some embodiments, any type of transducer may be positioned at or proximate a surface of the patient in a non-EIT configuration.

Thereafter, at 84, soft-field tomography excitations and/or non-soft-field tomography excitations are applied by the transducers. For example, ECG or EEG excitations may be applied in combination with EIT excitations, which may be performed simultaneously, concurrently or sequentially.

Thereafter, responses to the excitations are acquired at 86. It should be noted that the acquisition of the responses, such as by performing measurements at the transducers, may include filtering the responses. For example, the ECG signals may be filtered at a lower frequency than the EIT signals. In one embodiment, ECG signals may be low pass filtered with a cutoff frequency of about 500 Hz or less and EIT signals may be filtered with bandpass filters at the excitation carrier frequencies.

The responses are then used to generate measurement results 88, for example, to generate and display ECG data and EIT data based on predicted responses and using one or more EIT reconstruction algorithms. However, the EIT data may be based alternatively or additionally on different data, such as based on the excitations, boundary/surface data for the object, or prior EIT data, among others. Additionally, although the various embodiments are described in connection with electrical (current and voltage) excitation, other sources of excitation may be provided as described herein. Thus, the measured responses are not limited to electrical responses.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), field programmable gate arrays (FPGAs), graphical processing units (GPUs), digital signal processors (DSPs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The software or firmware may be, for example, FPGA code or DSP code.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon revlewmg the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first" "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A soft-field tomography sensing system comprising:
    a plurality of transducers configured for positioning at a surface of an object in a non-soft-field tomography configuration and configured to apply soft-field tomography excitations to the object;
    an interface;
    a processor communicating with the plurality of transducers via the interface, the processor configured to perform soft-field sensing using soft-field data acquired by the plurality of transducers, the soft-field data including responses to excitations; and
    a database which includes sets of said excitations and said responses, in combination, for each of the plurality of transducers, wherein the responses from the excitations are measured signals and the measured signals are filtered with bandpass filters at the excitation frequencies; wherein the processor frequency filters the non-soft-field sensing signals from the measured signals.

2. The soft-field tomography sensing system of claim 1, wherein the plurality of transducers comprises an electrocardiography (ECG) transducer set.

3. The soft-field tomography sensing system of claim 1, wherein the plurality of transducers comprises an electroencephalography (EEG) transducer set.

4. The soft-field tomography sensing system of claim 1, wherein the plurality of transducers comprises a non-soft-field sensing transducer set and at least one additional transducer.

5. The soft-field tomography sensing system of claim 1, wherein the plurality of transducers comprises a non-soft-field sensing transducer set and a soft-field sensing transducer set.

6. The soft-field tomography sensing system of claim 1, wherein the processor is further configured to perform soft-field sensing using soft-field data acquired at all of the plurality of transducers.

7. The soft-field tomography sensing system of claim 1, wherein the processor is further configured to perform soft-field sensing using soft-field data acquired at a subset of the plurality of transducers.

8. The soft-field tomography sensing system of claim 1, further comprising a connector configured to interface with at least one type of non-soft-field sensing transducer set and at least one type of soft-field sensing transducer set.

9. The soft-field tomography sensing system of claim 1, wherein the processor is further configured to perform soft-field sensing using soft-field data acquired by the plurality of transducers using at least one of Electrical Impedance Spectroscopy (EIS), Electrical Impedance Tomography (EIT), Diffuse Optical Tomography (DOT), Near InfraRed Spectroscopy (NIRS), thermography, elastography, microwave tomography or microwave spectroscopy.

10. The soft-field tomography sensing system of claim 1, wherein the processor is further configured to determine a property distribution of the object using the soft-field data including a distribution of one or more of electric conductivity, electric permittivity, magnetic permeability, optical absorbance, optical scattering, optical reflectivity, optical transmittance, elasticity, shear modulus or thermal conductivity.

11. The soft-field tomography sensing system of claim 1, further comprising a patient motioning device and wherein the plurality of transducers are configured for coupling to the patient monitoring device, wherein patient monitoring and soft-field sensing are performed one of simultaneously, concurrently or sequentially.

12. The soft-field tomography sensing system of claim 1, wherein the processor is configured to pre-compute at least one of the excitations or one or more predicted responses for the non-soft-field tomography configuration of the plurality of transducers that are selectable by a user.

13. The soft-field tomography sensing system of claim 1, wherein the processor is configured to dynamically compute at least one of the excitations or one or more predicted responses for the non-soft-field tomography configuration of the plurality of transducers.

14. A method for soft-field sensing, the method comprising:
positioning a plurality of transducers at a surface of an object in a non-soft-field tomography configuration to apply soft-field tomography excitations to the object;
obtaining measured signals from all or a subset of the plurality of transducers in response to the applied soft-field tomography excitations;
performing soft-field sensing using the measured signals acquired by the plurality of transducers; and
passively monitoring non-soft-field sensing signals while commanding a processor to frequency filter the non-soft-field sensing signals from the measured signals.

15. The method of claim 14, wherein positioning the plurality of transducers comprises positioning an electrocardiography (ECG) transducer set at the surface of the object.

16. The method of claim 14, wherein positioning the plurality of transducers comprises positioning an electroencephalography (EEG) transducer set at the surface of the object.

17. The method of claim 14, wherein positioning the plurality of transducers comprises positioning a non-soft-field sensing transducer set and at least one additional transducer at the surface of the object.

18. The method of claim 14, wherein positioning the plurality of transducers comprises positioning a non-soft-field sensing transducer set and a soft-field sensing transducer set at the surface of the object.

19. The method of claim 14, further comprising determining a property distribution in the object using at least one of Electrical Impedance Spectroscopy (EIS), Electrical Impedance Tomography (EIT), Diffuse Optical Tomography (DOT), Near InfraRed Spectroscopy (NIRS), thermography, elastography, microwave tomography or microwave spectroscopy.

20. The method of claim 14, further comprising determining a property distribution of the object, wherein the property distribution comprises a distribution of one or more of electric conductivity, electric permittivity, magnetic permeability, optical absorbance, optical scattering, optical reflectivity, optical transmittance, elasticity, shear modulus or thermal conductivity.

21. The method of claim 14, further comprising one of (i) pre-computing at least one of the excitations or one or more predicted responses for the non-soft-field tomography configuration of the plurality of transducers that are selectable by a user or (ii) dynamically computing at least one of excitations or predicted responses for the non-soft-field tomography configuration of the plurality of transducers.

22. A non-transitory computer readable storage medium for performing soft-field tomography using a processor, the computer readable storage medium including instructions to command the processor to:
obtain a plurality of measurement signals from all or a subset of a plurality of transducers positioned at a surface of an object in a non-soft-field tomography configuration, the plurality of measurement signals including first and second measurement signals; the first measurement signals including one or more responses to soft-field tomography excitations applied to the object by all or the subset of the plurality of transducers and the second measurement signals including non-soft-field sensing signals;
perform soft-field tomography using the first measurement signals acquired by the plurality of transducers;
monitor the second measurement signals; and
separate the first measurement signals from the second measurement signals by a step of filtering such that bandpass filters at the excitation frequencies are used to separate out the first measurement signals and a low pass filter is used to separate out the non-soft-field sensing signals.

23. The non-transitory computer readable storage medium of claim 22, wherein the instructions further command the processor to frequency filter non-soft-field sensing signals from the measurement signals.

24. The non-transitory computer readable storage medium of claim 22, wherein the instructions further command the processor to frequency filter soft-field sensing signals from the measurement signals.

25. The non-transitory computer readable storage medium of claim 22, wherein the plurality of transducers further comprise a transducer set configured for positioning at a surface of the object in a soft-field tomography configuration and the instructions further command the processor to obtain as the measurement signals at least one of soft-field data or non-soft-field data.

* * * * *

UNITED STATES PATENT AND TRADEMARK OFFICE
CERTIFICATE OF CORRECTION

| | | |
|---|---|---|
| PATENT NO. | : 8,983,578 B2 | Page 1 of 1 |
| APPLICATION NO. | : 13/406236 | |
| DATED | : March 17, 2015 | |
| INVENTOR(S) | : Ross et al. | |

It is certified that error appears in the above-identified patent and that said Letters Patent is hereby corrected as shown below:

IN THE SPECIFICATION

In Column 6, Line 39, delete "Lead 11" and insert -- Lead II --, therefor.

In Column 10, Line 14, delete "revlewmg" and insert -- reviewing --, therefor.

In Column 10, Line 22, delete ""first"" and insert -- "first," --, therefor.

Signed and Sealed this
Twentieth Day of October, 2015

Michelle K. Lee
*Director of the United States Patent and Trademark Office*